United States Patent
Vornbrock et al.

(10) Patent No.: US 7,637,161 B2
(45) Date of Patent: Dec. 29, 2009

(54) SUBSTRATE PENETRATING ACOUSTIC SENSOR

(75) Inventors: Theodore J. Vornbrock, Takoma Park, MD (US); Benjamin Dolgin, Alexandria, VA (US)

(73) Assignee: Raytheon UTD Inc., Springfield, VA (US)

( * ) Notice: Subject to any disclaimer, the term of this patent is extended or adjusted under 35 U.S.C. 154(b) by 439 days.

(21) Appl. No.: 11/406,361

(22) Filed: Apr. 19, 2006

(65) Prior Publication Data

US 2007/0256500 A1  Nov. 8, 2007

(51) Int. Cl.
*G01V 1/40* (2006.01)
(52) U.S. Cl. .............................. 73/587; 367/82; 181/102
(58) Field of Classification Search .................... 73/652, 73/654, 587
See application file for complete search history.

(56) References Cited

U.S. PATENT DOCUMENTS

| | | | |
|---|---|---|---|
| 2,790,968 A | 4/1957 | Cook et al. | |
| 3,888,636 A | 6/1975 | Sczerzenie et al. | |
| 3,906,781 A | 9/1975 | Vlasblom | |
| 4,282,588 A * | 8/1981 | Chanson et al. | 367/82 |
| 4,302,826 A * | 11/1981 | Kent et al. | 367/82 |
| 4,359,658 A * | 11/1982 | Cartier | 310/329 |
| 4,382,384 A | 5/1983 | Mitchell et al. | |
| 4,499,954 A | 2/1985 | Diggle | |
| 5,093,394 A | 3/1992 | Rees et al. | |
| 5,372,038 A | 12/1994 | Nicoletis | |
| 5,387,767 A * | 2/1995 | Aron et al. | 181/102 |
| 5,432,305 A | 7/1995 | Nelson | |
| 5,444,670 A | 8/1995 | Douglas | |
| 5,726,349 A | 3/1998 | Palmertree et al. | |
| 5,753,812 A | 5/1998 | Aron et al. | |
| 5,798,488 A * | 8/1998 | Beresford et al. | 181/102 |
| 5,935,485 A | 8/1999 | Tani et al. | |
| 5,996,412 A * | 12/1999 | Hansen | 73/514.34 |
| 6,357,283 B1 | 3/2002 | Welling et al. | |
| 6,405,135 B1 | 6/2002 | Adriany et al. | |
| 6,604,432 B1 | 8/2003 | Hamblen et al. | |
| 6,701,771 B2 | 3/2004 | Frost et al. | |
| 6,912,903 B2 | 7/2005 | Hamblen et al. | |
| 2006/0002232 A1* | 1/2006 | Shah et al. | 367/82 |

* cited by examiner

*Primary Examiner*—Hezron Williams
*Assistant Examiner*—Rose M Miller
(74) *Attorney, Agent, or Firm*—Dickstein Shapiro LLP

(57) ABSTRACT

An acoustic sensor configured to detect sound waves traveling through a substrate in which the acoustic sensor is embedded. The acoustic sensor includes a piezoelectric element and mass configured to receive and react to sound waves in three dimensions. Also, methods of using the acoustic sensor to receive sound waves traveling through a substrate.

25 Claims, 8 Drawing Sheets

SUBSTRATE PENETRATING ACOUSTIC SENSOR

The U.S. Government may have certain rights in this invention.

FIELD OF THE INVENTION

The present invention relates to a substrate penetrating, sub-surface monitoring acoustic sensor.

BACKGROUND OF THE INVENTION

Subterranean or other in-substrate acoustic sensors are known. Such devices have been used for metrology or the classification of the subterranean environment, for example, the identification of oil pocket location. Some such acoustic sensors have included piezoelectric instruments to detect subterranean sounds.

Conventional accelerometer sensors utilize a seismic mass that floats freely except for the attachment at a piezoelectric element. This configuration ensures that the device will be insensitive to vibrations, including those from sound waves, that strike the device off the primary axis, i.e., the line extending between the centers of gravity of the mass and the piezoelectric element. Accelerometers for metrology purposes are marketed by promoting this insensitivity to off-axis vibration, for example, that the device has a transverse (off-axis) sensitivity of 5% or less. It would be useful to have an acoustic sensor that could capture longitudinal as well as transverse vibrations for the acquisition of additional sound signal energy.

SUMMARY

The invention relates to an acoustic sensor suitable for insertion into and use in a subterranean or other in-substrate environment and method of using such a sensor. In an exemplary embodiment of the invention, the acoustic sensor includes a compressed piezoelectric element and a mass coupled to the device at a transverse energy coupler. This coupling allows the acoustic sensor to capture acoustic energy impacting both longitudinally and transversally for sound acquisition in three dimensions.

These other features of the invention can be better understood based on the following detailed description with reference to the accompanying drawings.

DETAILED DESCRIPTION

The invention relates to an acoustic sensor that can be forcibly embedded in a substrate and detect sound waves traveling through the substrate. The acoustic sensor can be used with a variety of substrate materials, for example, soil, rock, sand, man-made objects, and structures. The acoustic sensor has an accelerometer configuration having a piezoelectric sensor. It can detect sound waves in three dimensions by acquiring vibrations longitudinally, radially, and off-axis, with respect to a primary longitudinal axis running lengthwise through the sensor. The acoustic sensor can be tailored in materials and dimensions to be sensitive to a wide range of sound wavelengths.

Figure 1:
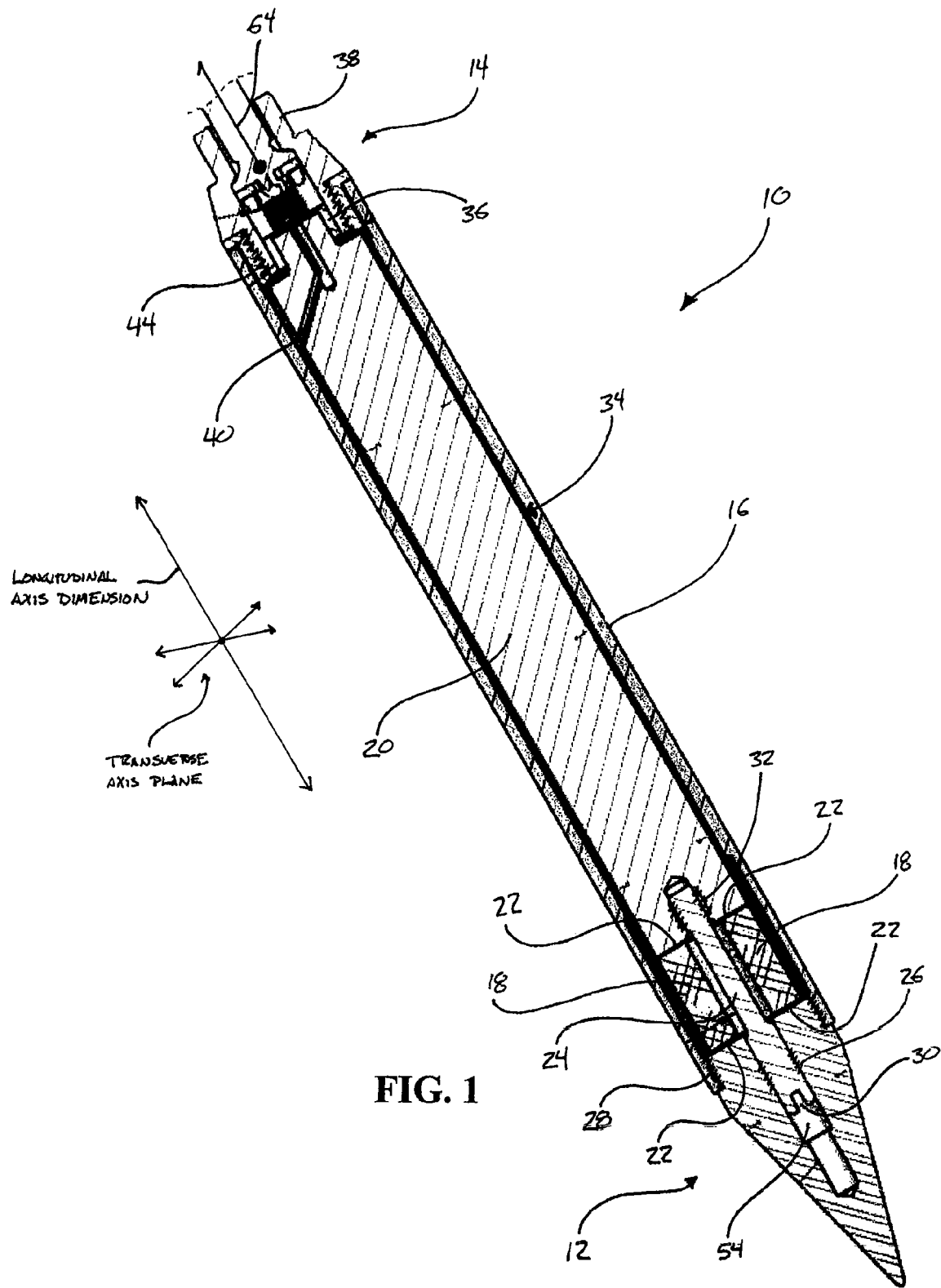
FIG. 1 is a cross-sectional view of an acoustic sensor constructed in accordance with the invention.

Preferred embodiments of the invention will now be explained with reference to the drawings, wherein like reference numbers indicate like features. FIG. 1 shows an acoustic sensor 10 which can be any size and can be made of many different materials. The sensor 10 is generally axially symmetrical. The cross-sectional plane of FIG. 1 extends through the axis of symmetry.

In a preferred embodiment, the sensor 10 is about 5 inches long from the tip of a conical head 12 to the end of a tail piece 14 and is well suited for sensing sound waves in the audible frequency range of about 5 Hz to about 20 kHz. By changing the dimensions and/or materials of the acoustic sensor 10, it can be tailored to sense sound waves of any frequency, e.g., from infrasonic frequencies relating to tectonic events to ultrasonic frequencies relating to insect infestation.

The acoustic sensor 10 shown in FIG. 1 includes a conical head 12, a tail piece 14, and a housing 16, which are configured to form an exterior body to support sensors within and to allow the acoustic sensor 10 to be forcibly embedded in a substrate 60 (FIG. 7), such as soil. The materials for the conical head 12, tail piece 14, and housing 16 should be suitable for the environment in which the acoustic sensor 10 is to be used, e.g., subterranean earth or other substrate, and should be relatively stiff and sturdy. So long as these features are incorporated into the conical head 12, tail piece 14, and housing 16, no specific materials are required and those known in the art, e.g., steel, aluminum, and titanium, can be used.

The conical head 12 can be connected to the housing 16 via threads 28. The tail piece 14 can be connected to the housing 16 via threads 44. Alternatively, other joining techniques can be used, such as welding, use of adhesives and others. Within the conical head 12, tail piece 14, and housing 16, the acoustic sensor 10 includes a piezoelectric element 18 and a seismic mass 20, which, together with electrodes 22 associated with the piezoelectric element 18, form an accelerometer sensor which can detect vibrations from sound waves impacting the acoustic sensor 10. A sleeve bearing 36 in the tail piece 14 couples the mass 20 with the housing 16. The sleeve bearing 36 allows for linear motion of the mass 20 (longitudinally), while also coupling transverse motions to the end of the mass 20.

The acoustic sensor 10 makes use of both on and off-longitudinal-axis vibrations made by sound waves by coupling them from the device conical head 12 and/or housing 16 into the piezoelectric element 18, which reacts against the inertia of the mass 20. While the acoustic sensor 10 can have up to 100% longitudinal sound wave sensitivity, it can also have about 30% or greater transverse sound wave sensitivity, which enables sound detection in three dimensions.

Figure 7:
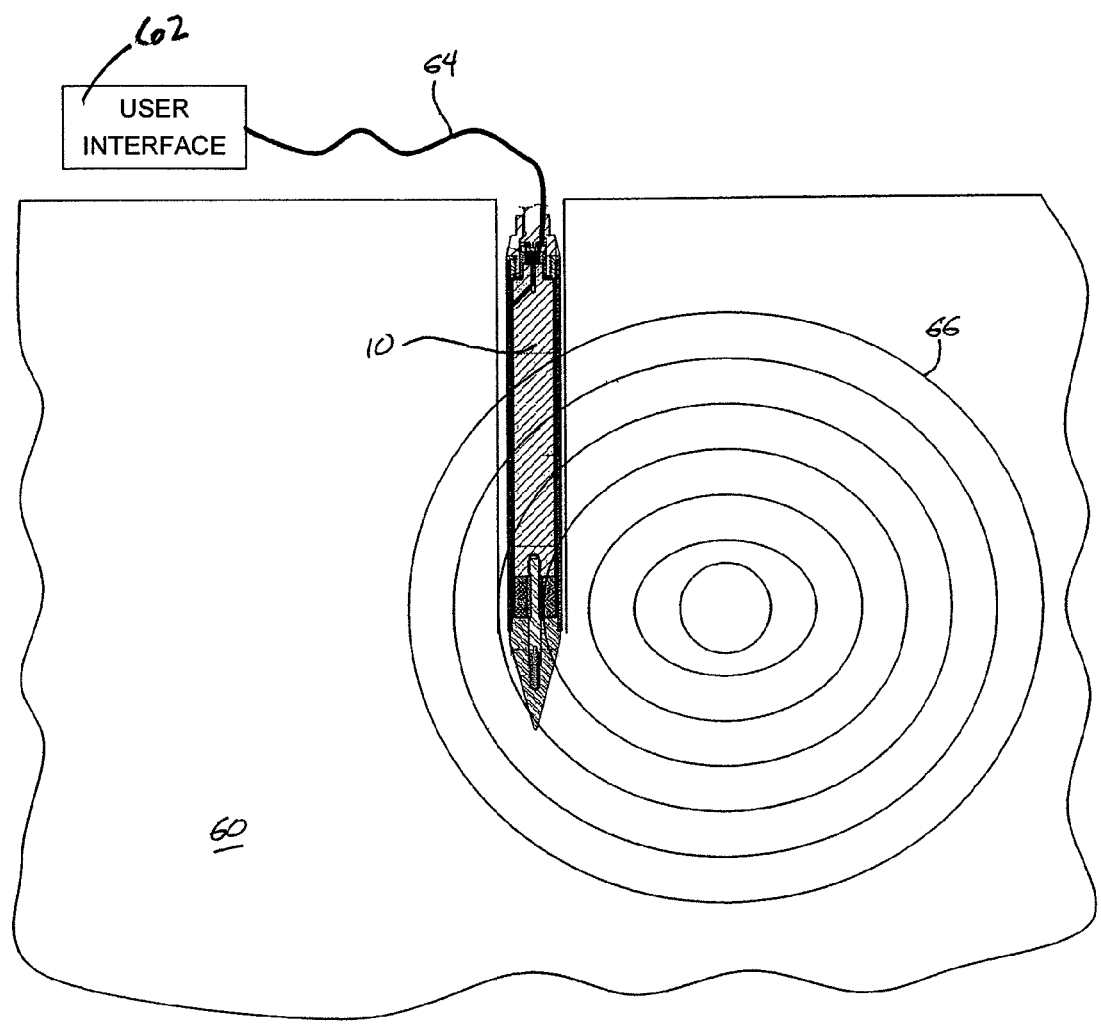
FIG. 7 is a schematic view showing the acoustic sensor of FIG. 1 in use within a substrate.

The electrodes 22 associated with the piezoelectric element 18 are electrically coupled to one or more wires 40, which can be a bifilar wire having two conductors, which runs the length of the housing 16, along the mass 20, to the tail piece 14. The wire 40 transmits signals from the piezoelectric element 18 to a transmission means 64, such as a cable or wireless transmitter, and thereby to a receiving means 62, such as a computer or amplifier (FIG. 7). A region 34 is provided between the housing 16 and the mass 20. This region 34 can be void of material or can be provided with means to couple the housing 16 with the mass 20 so as to further transmit off-axis, transverse vibrations to the mass 20. The coupling mechanism can be many different devices, such as a sleeve, a shearable material such as an elastomeric compound, or one or more o-rings.

Figure 2:
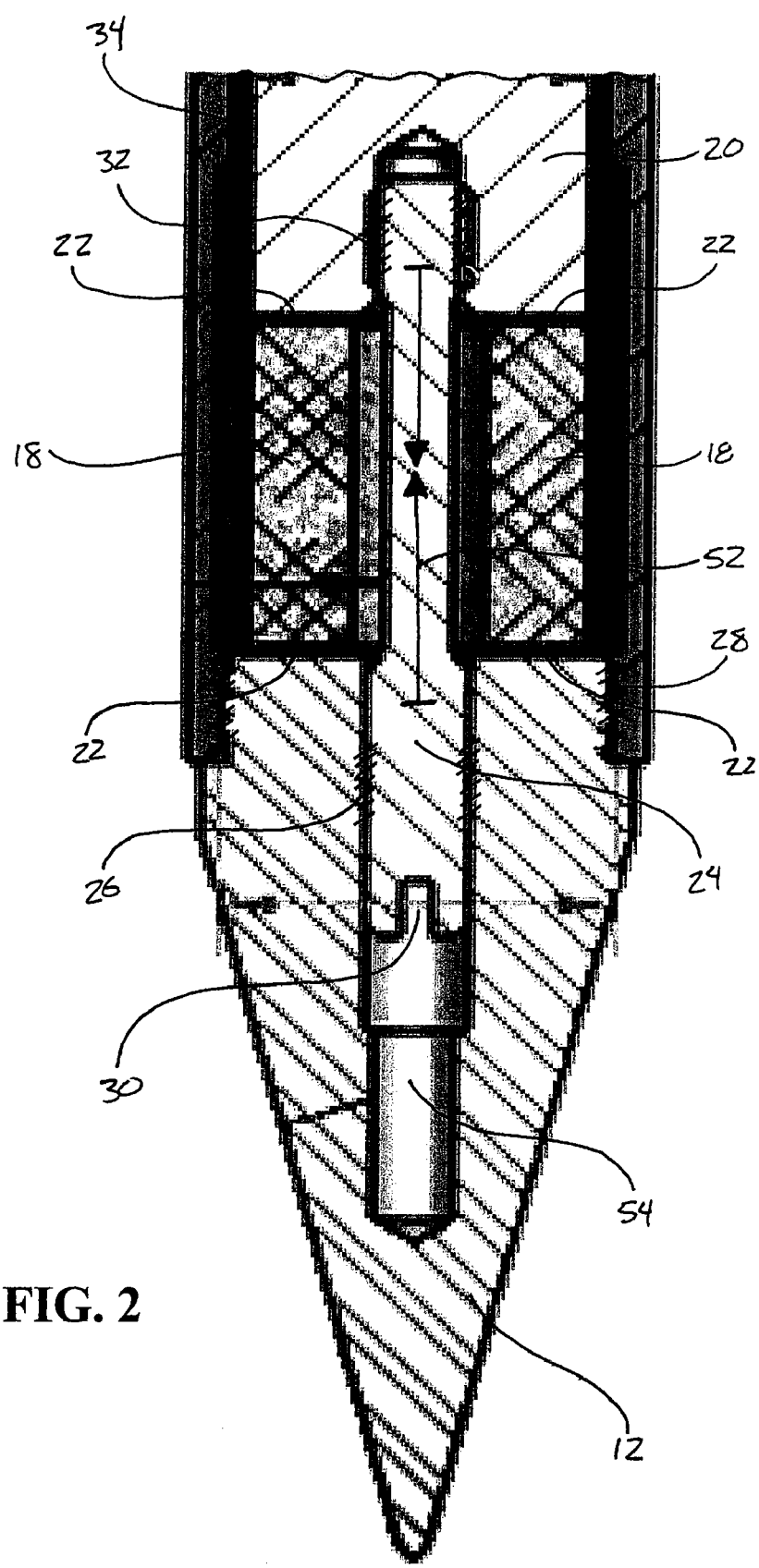
FIG. 2 is a partial cross-sectional view and FIG. 3 is a cross-sectional view of the leading and trailing ends of the sensor of FIG. 1, respectively, taken along the same cross-sectional plane of FIG. 1.

FIG. 2 shows an expanded view of the conical head 12 and the portion of the housing 16 with which it engages in accordance with the exemplary embodiment shown in FIG. 1. The conical head 12 is coupled to the mass 20 with a compression bolt 24, via threads 26 and 32. The mass 20 can be many different materials with high density and that allow rapid acoustical transmission so as to allow the mass 20 to be considered a lump acoustical element. Preferably, the mass 20 is a tungsten alloy, which has a density of about 18.5 g/cm$^3$.

The compression bolt 24 should be made of a sturdy material, such as steel, and can include an install notch 30, or other means, by which the compression bolt 24 can be secured within the mass 20. The compression bolt 24 is inserted through the ring-shaped piezoelectric element 18, which can be, for example, lead zirconate titanate ($Pb[Zr_xTi_{1-x}]O_3$, where x=0.52, also known as lead zirconium titanate), which is a ceramic perovskite material that develops a voltage difference across two of its faces when compressed. Other piezoelectric materials, such as, for example, quartz crystal, bismuth titanate, lead nickel niobate, and others, can be used also. When lead zirconate titanate is used as the piezoelectric element 18, it can be modified to have a higher dielectric constant, which is advantageous if the sensor is to be very small. Electrodes 22 are positioned on both sides of the piezoelectric element 18 for capturing charge generated upon varying the compression of the element 18. After insertion through the piezoelectric element 18, the compression bolt 24 can be screwed into the mass 20 via the threads 32.

When the conical head 12 is attached to the housing 16 at threads 28, it also engages the compression bolt 24 at threads 26. As the conical head 12 is attached to the housing 16, tension is added to the compression bolt 24 and the piezoelectric element 18 is compressed 52 between the mass 20 and the conical head 12. Generally, about 5 MPa (mega pascal) to about 40 MPa is sufficient compression 52 without being excessive, with about 10 MPa to about 25 MPa being preferred. This compression 52 protects and sensitizes the piezoelectric element 18 for operation of the acoustic sensor 10. The compression 52 is designed to keep the piezoelectric element 18 in intimate acoustical contact with the mass 20 and the conical head 12 and prevent the piezoelectric element 18 from going into tension at any time. The compression 52 couples the conical head 12 to the sensing features of the acoustic sensor 10 and enables sound detection from three dimensions, e.g., longitudinally and off-axis relative to the length of the sensor 10. Too much compression 52 can cause de-poling of the piezoelectric element 18, which would prevent the element 18 from functioning. The amount of acceptable compression depends on the material properties of the piezoelectric element 18.

Figure 3:
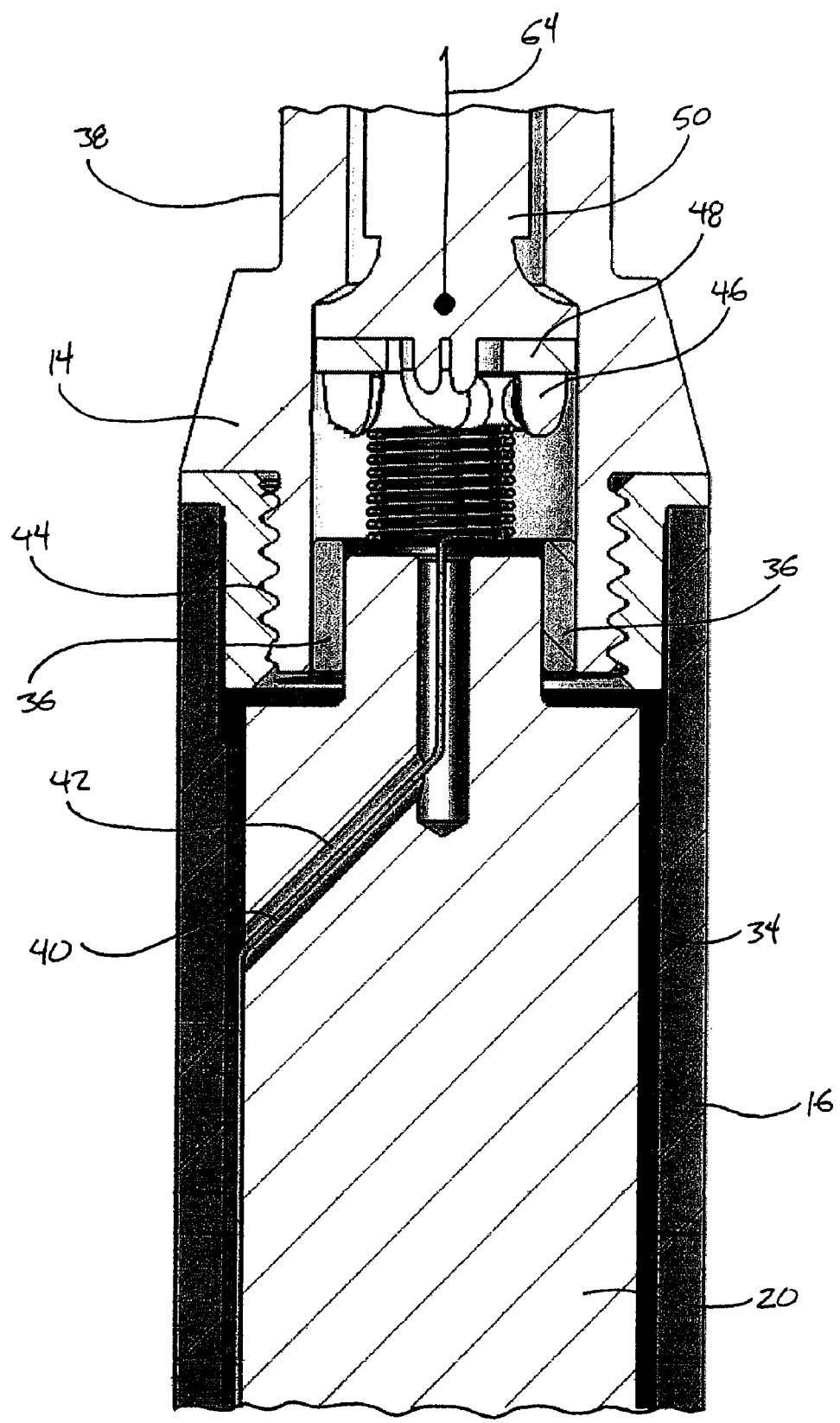

FIG. 3 shows an expanded view of the tail piece 14 and the portion of the housing 16 with which the tail piece 14 engages in accordance with the exemplary embodiment shown in FIG. 1. The tail piece 14 engages the housing 16 at threads 44. An attachment means 38 can be provided, for example in the form of wrench flats, for engaging a tool for embedding the acoustic sensor 10 in a substrate. Proximate the threads 44, the tail piece 14 includes a sleeve bearing 36, which supports the mass 20.

The sleeve bearing 36 is a transverse energy coupler and can be made of a variety of materials, but is preferably a polyimide-polyamide blend. Alternatively, this transverse energy coupler can be a metal, for example, bronze or cast iron, or plastic, such as nylon, delrin, and polyethylene. Different materials can transmit or attenuate acoustical energy differently and it may be desired to use specific sleeve bearing 36 materials for receiving certain acoustical wavelengths. Generally, the sleeve bearing 36 can be any material that is stiff in compression and non-lossy acoustically.

A hole 42 can be provided through the mass 20 for passage of the wire 42. The wire 42 is collected in the tail piece 14 and is connected to solder points 46, or other connection means, and thereby to a printed circuit board 48, or other processor means. The circuit board 48 can include an amplifier for the signals produced by the piezoelectric element 18. The signals can be output from the acoustic sensor 10 via a transmission means 64, for example a cable or powered wireless transmitter, provided within a void 50, to some user interface means 62, such as a computer or amplifier (FIG. 7).

Figure 4:
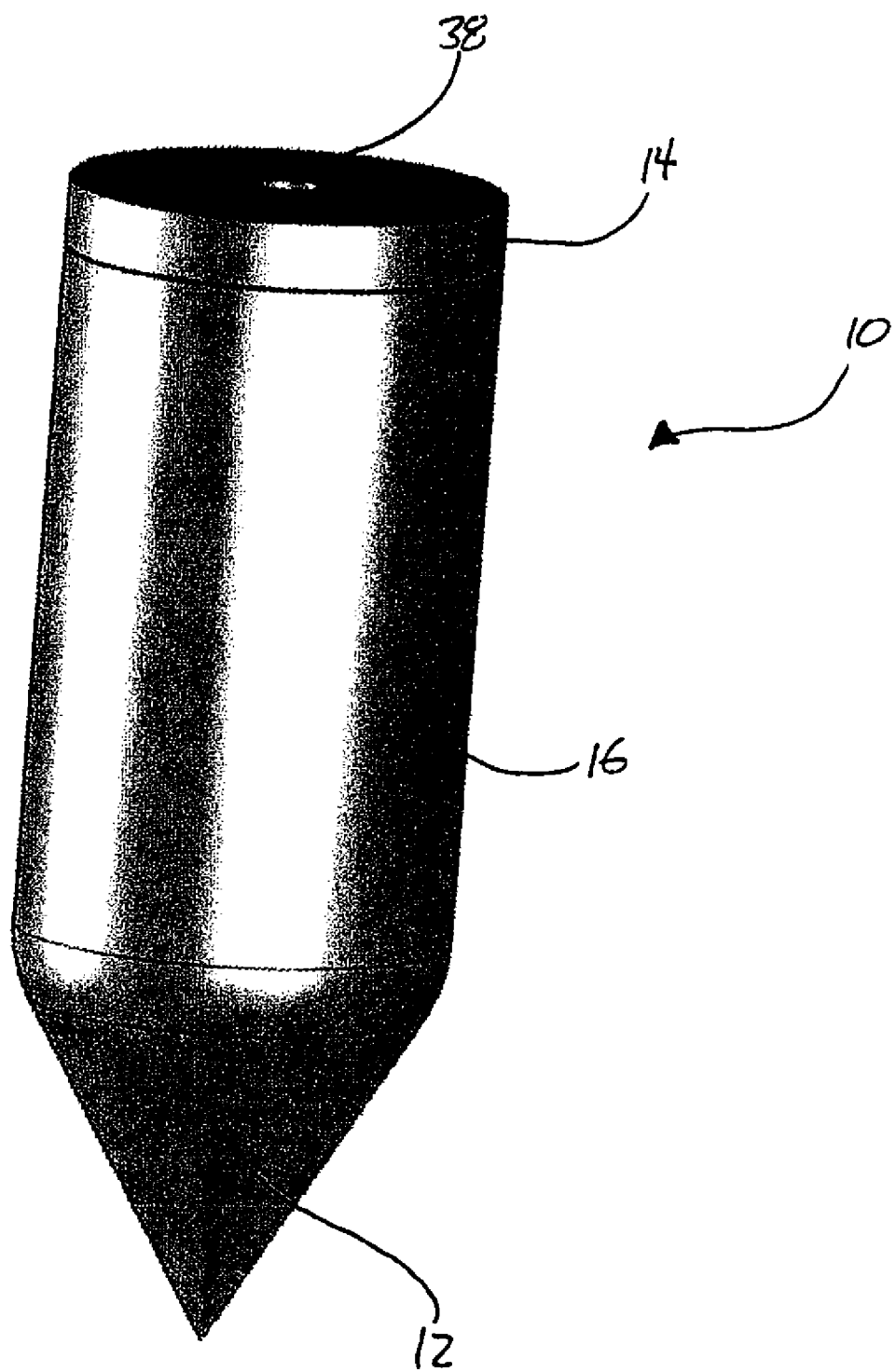
FIG. 4 is a perspective view of the sensor of FIG. 1.

FIG. 4 shows an exterior view of the acoustic sensor 10. As shown, the acoustic sensor 10 has a hard conical head 12, housing 16, and tail piece 14. An attachment means 38 is shown on the tail piece 14. As shown, the bullet-shape of the acoustic sensor 10 provides for insertion into a variety of substrates and the dimensions of this shape can be tailored to fit the substrate, as well as the sound wave frequency desired to be sensed.

Figure 5:
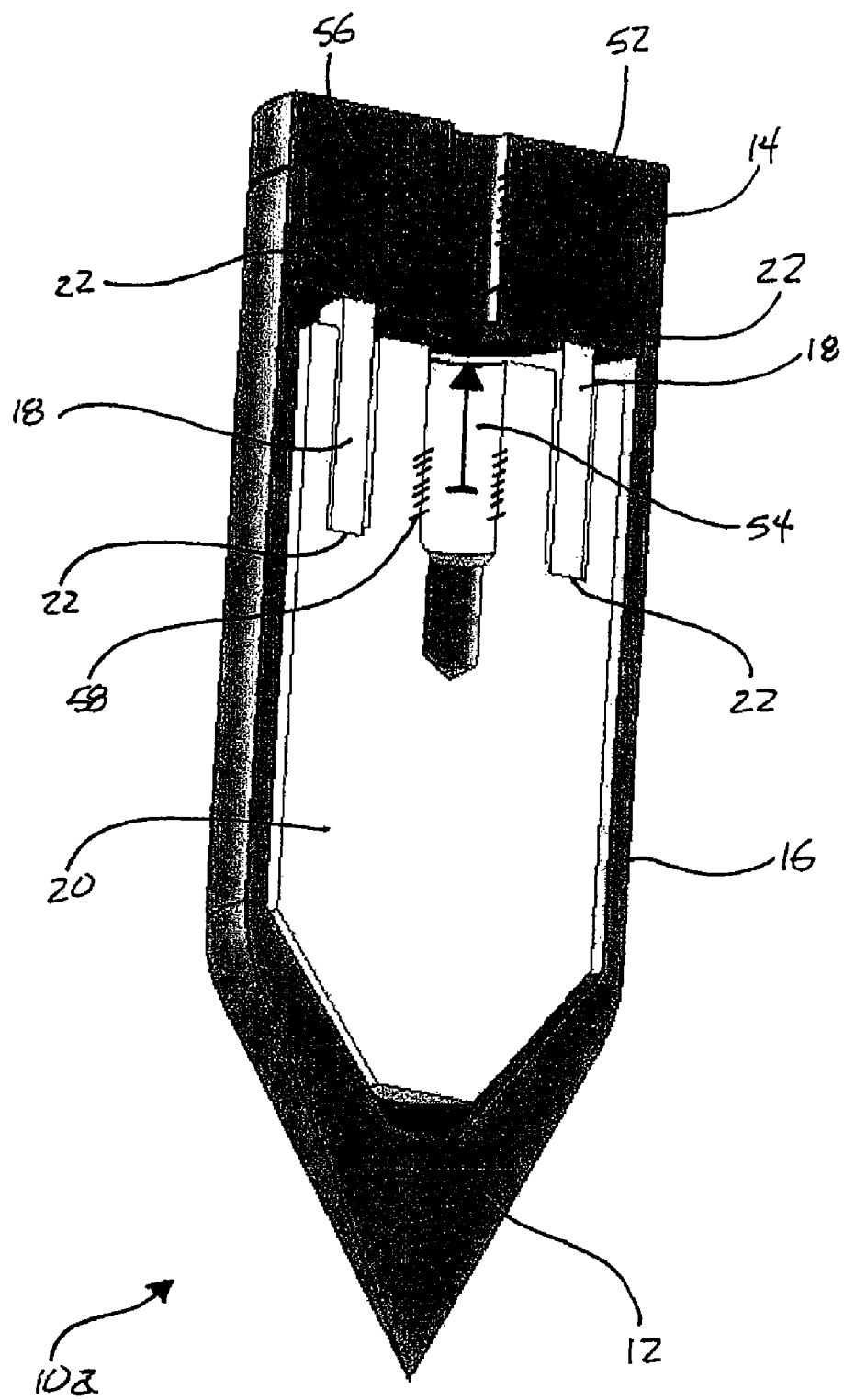
FIGS. 5 and 6 are cross-sectional views of other acoustic sensors constructed in accordance with the invention.

FIG. 5 shows an alternative exemplary embodiment in accordance with the invention. In this embodiment of the acoustic sensor 10a, the conical head 12 is not directly coupled to the mass 20. The tail piece 14 is coupled to the mass 20 by a compression bolt 24, like that shown in FIG. 1, which is provided within the void 54 shown in FIG. 5. As with the embodiment shown in FIG. 1, in this embodiment the compression bolt 24 engages threads 58 in the mass 20. The tail piece 14 also has threads 14, which engage the compression bolt 24 and apply tension thereto to compress 52 the piezoelectric element 18, which can fit inside the mass 20. Electrodes 22 are provided in this embodiment as well.

Figure 6:
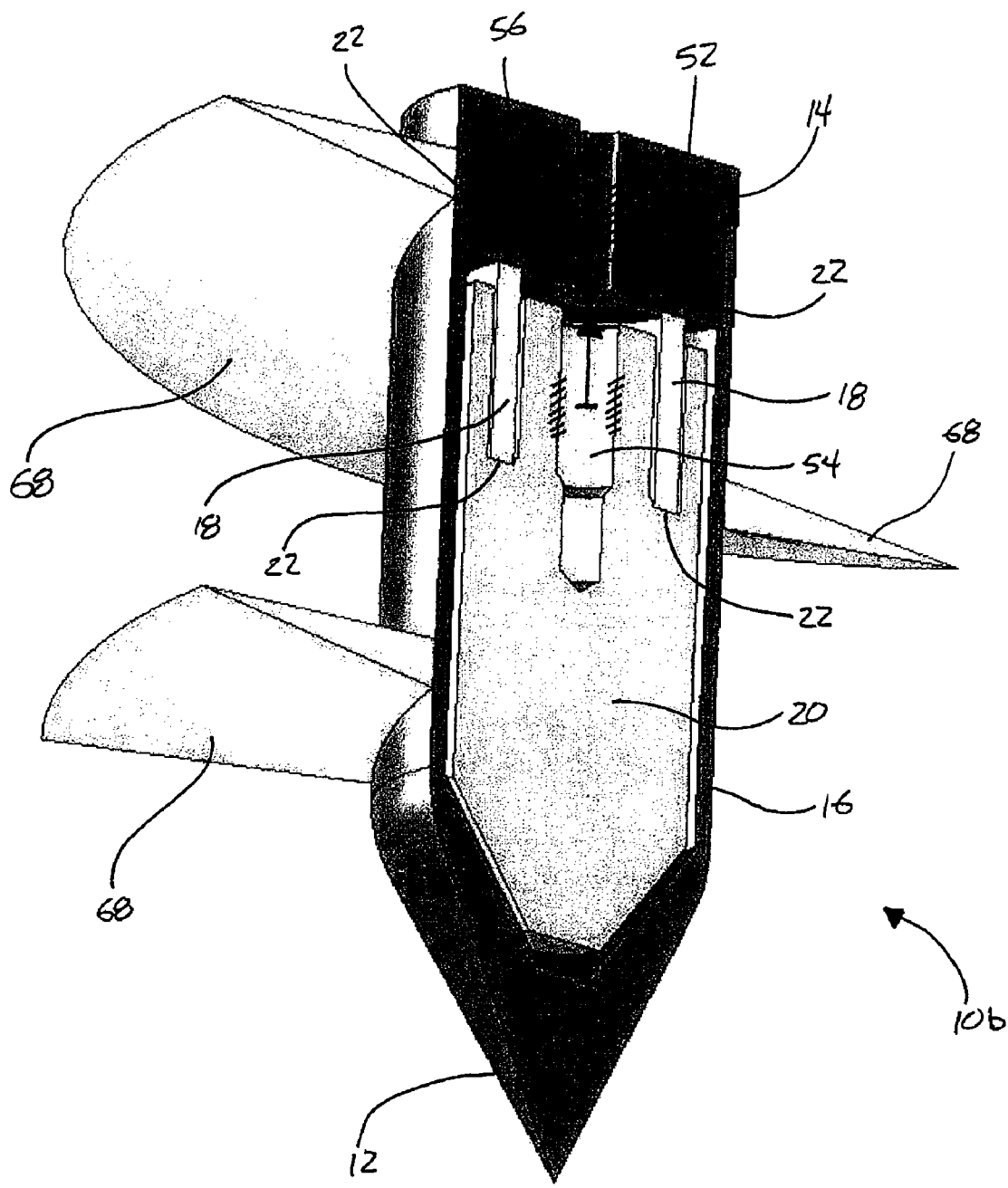

FIG. 6 shows an alternative exemplary embodiment in accordance with the invention. The acoustic sensor 10b includes a substrate engagement means 68, which can be adapted for use with any other embodiment of the invention. As shown, the substrate engagement means 68 is an auger shaped protrusion on the housing 16 of the acoustic sensor 10b. However, the substrate engagement means 68 can be in a variety of forms. For example, the substrate engagement means 68 could be a spiral thread, a friction surface, fins, hooks, or any other device suitable for engaging or embedding the acoustic sensor 10b with or in a substrate.

Figure 8:
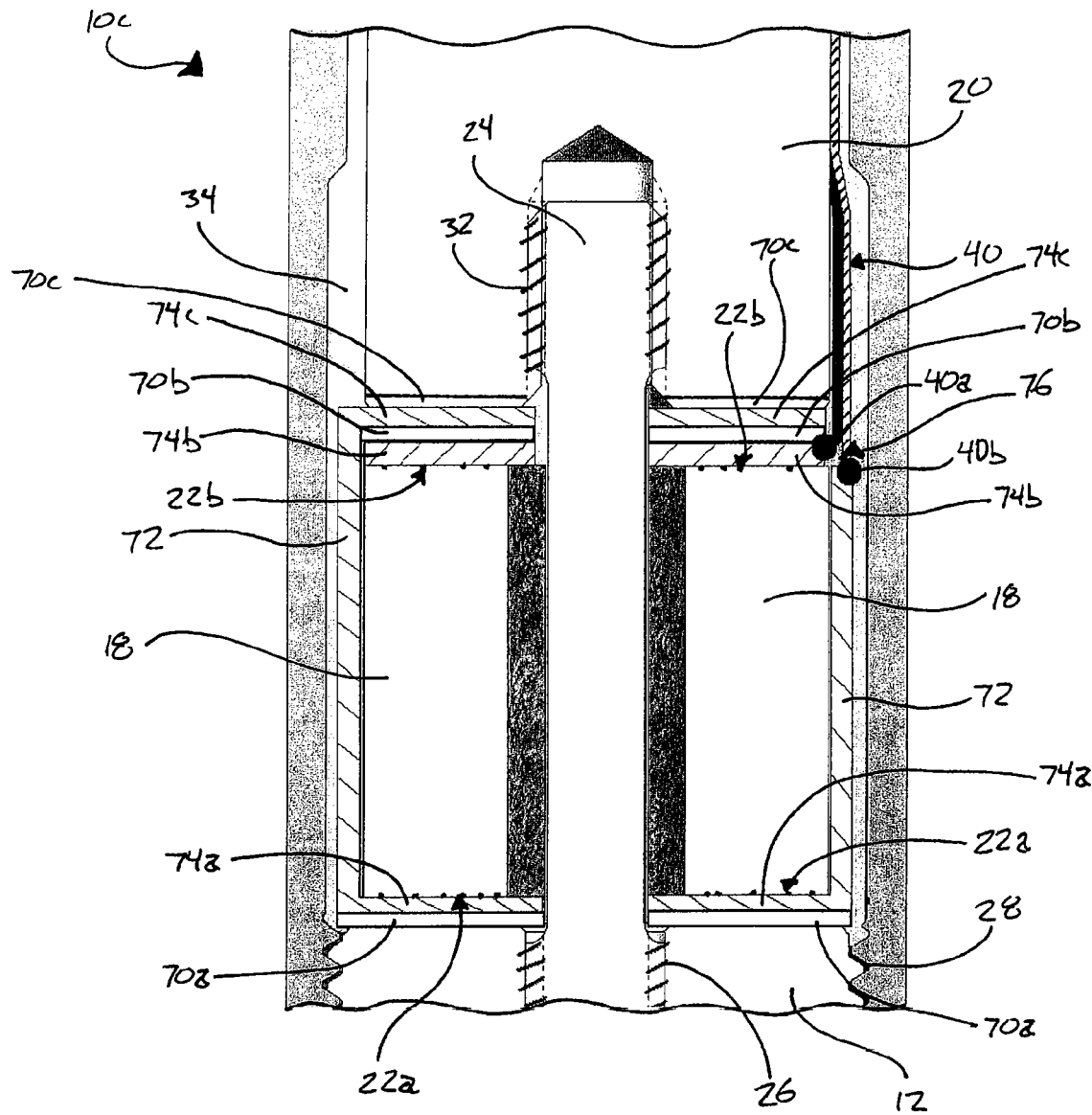
FIG. 8 is a cross-sectional view of an acoustic sensor constructed in accordance with the invention.

In another exemplary embodiment as shown in FIG. 8, the acoustic sensor 10c has a piezoelectric element 18, which can have electrode surfaces 22a and 22b that can be integral to the piezoelectric element 18 and can be formed by screen-printing or sputtering metal or another conductor. As in other embodiments (FIGS. 1 and 2), the piezoelectric element 18 is compressed between a conical head 12 and a mass 20. In the embodiment shown in FIG. 8, components are provided for electrical shielding of the piezoelectric element 18 from electro-magnetic interference (EMI).

The shielding components are included in the region compressed by the compression bolt 24, between the conical head 12 and the mass 20. The shielding components can include a thin, stiff, electrically insulating washer 70a, which can be made of mica or a ceramic, for example, and a conductive tubular shield 72 electrically attached to a bottom conductive washer 74a and the electrode surface 22a. The shielding components can further include an upper conductive washer 74b over the electrode surface 22b, an insulating washer 70b over the upper conductive washer 74b, a conductive washer 74c over the insulating insulating washer 70b, an insulating washer 70c over the conductive washer 74c, and the mass 20.

This shielding component arrangement surrounds the piezoelectric element 18 with a layer of conductive material, forming a faraday cage. EMI currents enter this faraday cage, since the shield 72 and conductive washers 70a, 70b, and 70c are shorted to ground, rather than coupling into the signal output of the piezoelectric element 18 at electrode surface 22b. EMI currents exit the faraday cage at a gap 76. The bifilar wire 40 can include a signal wire 40a connected to a conductive washer 74b and electrode surface 22b and a shield wire 40b connected to the shield 72.

FIG. 7 shows an exemplary embodiment of an acoustic sensor 10 in use in accordance with the invention. The acoustic sensor 10 is embedded in a substrate 60. This may be accomplished in a variety of ways, for example, by screwing or pushing it into the substrate 60. The acoustic sensor 10 is connected to a user interface, such as the computer 62 shown, via a cable 64 or other means, such as a wireless transmitter. The acoustic sensor 10 can receive sound waves 66 traveling through the substrate 60 in three dimensions and transmit signals of the sounds to the user interface. The types of substrates 60, environments, and uses of the acoustic sensor 10 are not limited to any specific types and the acoustic sensor 10 can be used in any circumstance where sound waves 66 travel through a substrate 60.

Various embodiments of the invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed as new and desired to be protected by Letters Patent of the United States is:

1. An acoustic sensor, comprising:
    a supportive body configured to penetrate a substrate in a longitudinal direction;
    a piezoelectric element located within said body;
    a mass adjacent said piezoelectric element, said mass being located within said body; and
    a coupling device located within said body, said coupling device being configured to couple the mass to the supportive body, said coupling device allowing vibration of said mass relative to said body in said longitudinal direction and in a transverse direction, said transverse direction being transverse to said longitudinal direction; and
    wherein said piezoelectric element is arranged to sense said vibration of said mass relative to said body in said transverse direction, and to thereby generate signals representative of acoustic energy transmitted through said substrate and into said body in said transverse direction.

2. The acoustic sensor of claim 1, wherein said supportive body comprises a conical head, a housing, and a tail piece, and wherein said conical head and said piezoelectric element are axially symmetric about a longitudinal axis aligned in said longitudinal direction.

3. The acoustic sensor of claim 2, wherein said conical head is coupled to said mass at a compression bolt and said housing is coupled to said mass at a sleeve bearing, and wherein said compression bolt is aligned with said longitudinal axis.

4. The acoustic sensor of claim 1, wherein said piezoelectric element is compressed between said mass and a head with a compression bolt.

5. The acoustic sensor of claim 1, wherein said piezoelectric element is compressed between said mass and a tail piece with a compression bolt.

6. The acoustic sensor of claim 1, wherein said piezoelectric element is compressed at between about 5 MPa and about 40 MPa.

7. The acoustic sensor of claim 6, wherein said piezoelectric element is compressed at between about 10 MPa and about 25 MPa.

8. The acoustic sensor of claim 1, wherein said mass has a density of about 18.5 g/cm$^3$.

9. The acoustic sensor of claim 1, wherein said mass is a tungsten alloy.

10. The acoustic sensor of claim 1, further comprising an electrode between said mass and said piezoelectric element.

11. The acoustic sensor of claim 1, wherein said sensor is configured to sense sound waves transmitted through said substrate.

12. The acoustic sensor of claim 11, wherein said sensor is configured to sense sound waves in three dimensions.

13. The acoustic sensor of claim 1, wherein said coupling device comprises a sleeve bearing.

14. The acoustic sensor of claim 13, wherein said sleeve bearing comprises a polyimide-polyamide blend.

15. The acoustic sensor of claim 1, wherein said mass has a length with a first end and a second end, wherein said piezoelectric element is proximate said first end and said coupling device is proximate said second end.

16. The acoustic sensor of claim 1, comprising a longitudinal axis aligned in said longitudinal direction, wherein said piezoelectric element, said mass, and said coupling device are configured to sense acoustic energy impacting said supportive body from said longitudinal and transverse directions.

17. The acoustic sensor of claim 1, further comprising means for coupling a housing to said mass.

18. The acoustic sensor of claim 17, wherein said means for coupling a housing to said mass comprises a device selected from the group consisting of a sleeve, a shearable material, and at least one o-ring.

19. The acoustic sensor of claim 1, wherein said piezoelectric element and said mass are configured to sense acoustic energy between about 5 Hz and about 20 kHz.

20. The acoustic sensor of claim 1, further comprising substrate engagement means.

21. The acoustic sensor of claim 1, further comprising means for shielding the piezoelectric element from electromagnetic interference.

22. A method of sensing acoustic energy, comprising:
    providing an acoustic accelerometer sensor with a housing, a mass, and a ring-shaped piezoelectric element, said housing, said mass, and said ring-shaped piezoelectric element being axially symmetrical about a longitudinal axis, and configuring said acoustic sensor to be sensitive to acoustic energy directed toward said acoustic sensor along said longitudinal axis, and configuring said acoustic sensor to be sensitive to transverse acoustic energy directed toward said acoustic sensor through a substrate in a transverse direction;
    causing said acoustic sensor to penetrate a substrate in a longitudinal direction, while said longitudinal axis of said acoustic sensor is aligned with said longitudinal direction, and thereby embedding said acoustic sensor in said substrate, and wherein said transverse direction is transverse to said longitudinal direction;

transmitting said transverse acoustic energy through said housing and into said mass. such that said mass vibrates relative to said housing in said transverse direction, and thereby causing said piezoelectric element to generate information relating to said transverse acoustic energy; and transmitting said information relating to said transverse acoustic energy from said acoustic sensor to a user interface.

23. The method of claim 22, further comprising a coupling device configured to couple the mass to the housing.

24. The method of claim 23, wherein said sensor comprises a conical head having a tip for penetrating the substrate, and wherein said housing encloses said mass and said piezoelectric element, and wherein said sensor comprises a tail piece having an end opposite to said conical head, said housing being located between said conical end and said tail piece, and wherein the acoustic sensor is about five inches long from said tip of said conical head to said end of said tail piece.

25. The method of claim 23, further comprising providing a means for shielding the piezoelectric element from electromagnetic interference.

* * * * *

UNITED STATES PATENT AND TRADEMARK OFFICE
CERTIFICATE OF CORRECTION

PATENT NO.      : 7,637,161 B2                    Page 1 of 1
APPLICATION NO. : 11/406361
DATED           : December 29, 2009
INVENTOR(S)     : Vornbrock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 693 days.

Signed and Sealed this

Ninth Day of November, 2010

David J. Kappos
*Director of the United States Patent and Trademark Office*